(12) United States Patent
Caccia et al.

(10) Patent No.: US 7,763,751 B2
(45) Date of Patent: Jul. 27, 2010

(54) HYDROXYLAMINE DERIVATIVES

(75) Inventors: Carla Caccia, Cardano Al Campo (IT); Laura Girola, Gerenzano (IT); Petra Karin Kaltofen, Milan (IT); Daniele Losi, Rovellasca (IT); Patricia Salvati, Arese (IT); Enrico Selva, Gropello Cairoli (IT); Florian Thaler, Merano (IT)

(73) Assignees: Newron Pharmaceuticals S.p.A., Bresso (IT); Vicuron Pharmaceuticals Inc., Wilmington, DE (US)

( * ) Notice: Subject to any disclaimer, the term of this patent is extended or adjusted under 35 U.S.C. 154(b) by 244 days.

(21) Appl. No.: 10/582,141

(22) PCT Filed: Dec. 10, 2004

(86) PCT No.: PCT/EP2004/014077

§ 371 (c)(1),
(2), (4) Date: Jul. 5, 2006

(87) PCT Pub. No.: WO2005/058800

PCT Pub. Date: Jun. 30, 2005

(65) Prior Publication Data

US 2007/0049643 A1 Mar. 1, 2007

(30) Foreign Application Priority Data

Dec. 11, 2003 (EP) ................... 03028441

(51) Int. Cl.
*C07C 239/00* (2006.01)
*A61K 31/13* (2006.01)

(52) U.S. Cl. ............ 564/300; 514/645; 560/24; 560/109; 560/312; 562/621

(58) Field of Classification Search ......... 514/645; 424/320, 324; 560/24, 109, 312; 562/621; 564/300
See application file for complete search history.

(56) References Cited

U.S. PATENT DOCUMENTS 3,184,510 A * 5/1965 Levy .................. 564/300

FOREIGN PATENT DOCUMENTS

| GB | 1 062 299 | | 3/1967 |
| GB | 1062299 | * | 3/1967 |
| WO | WO 99/62505 | | 12/1999 |
| WO | WO 01/30979 | | 5/2001 |

OTHER PUBLICATIONS

Morgan, et al., "Synthesis of some N-oxygenated products of 3,4-dimethoxyampethamine and its N-alkyl Derivatives", 1975, Tetrahedron, vol. 31, pp. 2598-2599.*

Korting, G.W. et al., Pharmacology of the experimental pilomotor reaction, 1954, Arzneimittel-Forschung, 4, pp. 63-67 (English abstract from STN, caplus database).*
Davidson, M.W., Epinephrine (Adrenalin), 1995-2000, (abstract).*
Demaimay, R. et al., Late treatment with polyene antibiotics can prolong the survival time of scrapie-infected animals, 1997, Journal of Virology, vol. 71, No. 12, pp. 9685-9689.*
Doh_ura, K. et al. Treatment of transmissible spongiform encephalopathy by intraventricular drug infusion in animal models, 2004, Journal of Virology, vol. 78, No. 10, pp. 4999-5006.*
Karpuj, M. et al., Prolonged survival and decreased abnormal movements in transgenic model of Huntington disease, with administration of the transglutaminase inhibitor cystamine, 2002, Nature Medicine, vol. 8, No. 2, pp. 143-149.*
Luis, C. A. et al., Difuse Lewy body disease: Clinical, pathological, and neuropsychological review, 1999, Neuropsychology Review, vol. 9, No. 3, pp. 137-150.*
Pepys, M.B. et al., Pathogenesis, diagnosis and treatment of systemic amyloidosis, 2001, Phi. Trans. Royal Society London B, vol. 356, pp. 203-211.*
Quinn, N., Fortnghtly Review: Drug treatment of Parkinson's disease, 1995, British Medical Journal (BMJ), March, pp. 575-579.*
Ross, C. et al., protein aggregation and neurodegenerative disease, 2004, Nature Medicine, Review, pp. S10-S17.*
P.H. Morgan et al.: "Synthesis of Some N-Oxygenated Products of 3,4-Dimethoxyamphetamine and its N-Alkyl Derivatives" Tetrahedron, (Incl Tetrahedron Reports), vol. 31, 1975, pp. 2595-2601, XP002279539 Oxford GB p. 2598, col. 2, paragraphs 3-4; p. 2600, col. 2, table 1, compound 6.

* cited by examiner

*Primary Examiner*—Daniel M Sullivan
*Assistant Examiner*—Yate' K Cutliff
(74) *Attorney, Agent, or Firm*—Young & Thompson

(57) ABSTRACT

This invention is related to hydroxylamino derivatives of the general formula (I) wherein n is 0, 1 or 2; $R^1$ and $R^2$, independently of each other, are H, OH or $OCH_3$; $R^3$ is H or $CH_3$; $R^4$ is H, $C_1$-$C_3$ straight or branched alkyl or, together with $R^3$, forms a five to seven-membered carbocyclic ring; and $R^5$ and $R^6$, independently of each other, are H or $C_1$-$C_5$ straight or branched alkyl and the pharmaceutically acceptable salts or prodrug thereof, for the preparation of medicaments useful for the prevention, treatment and diagnosis of CNS degenerative disorders related to protein misfolding and/or misaggregation. The invention also relates to novel compounds included in formula (I), to a method for preparing said compounds and to pharmaceutical compositions containing them.

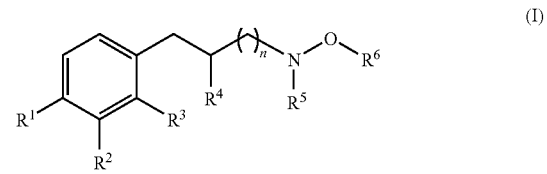

(I)

3 Claims, No Drawings

HYDROXYLAMINE DERIVATIVES

This invention is related to hydroxylamino derivatives of the following general formula (I)

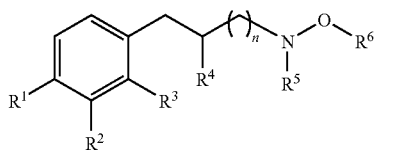

wherein
n is 0, 1 or 2;
$R^1$ and $R^2$, independently of each other, are H, OH or $OCH_3$;
$R^3$ is H or $CH_3$;
$R^4$ is H, $C_1$-$C_3$ straight or branched alkyl or, together with $R^3$, forms a five to seven-membered carbocyclic ring;
and $R^5$ and $R^6$, independently of each other, are H or $C_1$-$C_5$ straight or branched alkyl
and the pharmaceutically acceptable salts or prodrug thereof, for the preparation of medicaments useful for the prevention, treatment and diagnosis of central and peripheral degenerative disorders related to protein misfolding and/or misaggregation.

The invention also relates to novel compounds included in the above formula (I), to a method for preparing said compounds and to pharmaceutical compositions containing them.

FIELD OF INVENTION

The present invention relates to novel compounds, pharmaceutical compositions containing said compounds and their use in the treatment and diagnosis of central and peripheral nervous system degenerative disorders such as those caused by formation of fibrils of beta-amyloid peptide, alpha-synuclein, prion protein and huntingtin, Alzheimer's Disease, Lewy body disease, Parkinson's Disease, spongiform encephalopathies, Huntington's Disease and systemic AA amyloidosis including the primary amyloidosis of the peripheral nervous system.

BACKGROUND OF THE INVENTION

In recent years it has been found that several neurodegenerative disorders are caused by protein misfolding and/or misaggregation.

One of the most important and initial step of Alzheimer's disease (AD), for instance, involves proteolytic cleavage of APP (amyloid precursor protein,) releasing short 40, 42 and 43 aa peptides (beta amyloid 1-40, 1-42, and 1-43). The degeneration of neurons is due to polymerization of beta-amyloid peptides (Aβ) and subsequent neuronal deposit (amyloid). Monomeric Aβ is a product of normal metabolism and is not toxic to neuronal cells. As it forms multimeric and polymeric assemblies of itself, Aβ acquires potent toxicity for neuronal cells. Inhibition of this polymerization process has thus been identified as a potential approach to the treatment of AD and all other related pathologies where the anatomopathological hallmark is the presence of Aβ deposit.

Amyloid like-disorders might be far more widespread than previously thought, and might include many common neurodegenerative and neuromuscular pathologies, as well as prion disease. Prion diseases can be either sporadic or infectious, and until recently were not known to be associated with protein misfolding and deposition. Prions are composed solely of a misfolded prion protein ($PrP^{Sc}$) isoform of a glicolipid-anchored host protein. Patients with prion diseases develop progressive neurologic dysfunction. Prion diseases are invariably fatal and no effective therapy exists till now. Compounds that inhibit $PrP^{Sc}$ formation including Congo red, are effective in scrapie-infected cultured cells.

It has also been found that the formation of intraneuronal deposits called Lewy bodies and Lewy neurites is due to aggregates of another protein, alpha-synuclein, whose misfolding and misaggregation is also believed to be one of the causes of both AD and Parkinson's disease.

U.S. Pat. No. 3,184,510 discloses N-alkoxy and N-hydroxyphenylethylamines of the following general formula:

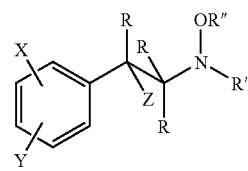

wherein
X and Y, independently of each other, are H, OH or $OCH_3$;
Z is H or OH;
R is H or $CH_3$;
R' is H, $CH_3$, $C_2H_5$, $C_3H_7$ or i-$C_3H_7$;
R" is $CH_3$, $C_2H_5$, $C_3H_7$ or i-$C_3H_7$
and their use for sustaining and/or raising blood pressure, their use as local vasoconstrictors and/or in the relaxation of the bronchial smooth muscles and of the intestinal tract, in pupil dilation and in the stimulation of adrenergic nerves. No CNS activity was disclosed.

GB 1,062,299 discloses 3,4-dihydroxyphenyl-propane derivatives of the general formula Ar—$CH_2$—C($CH_3$)—NH(OR), wherein Ar is 3,4-dihydroxyphenyl and R is H or $C_1$-$C_8$ alkyl, as hypertensive agents.

Major, R. T. and Ohly, K. W. J. (Med. and Pharmaceut. Chem. 1961, 4, 51-65) described the synthesis of N-alkoxy-N-(2-phenyl)-isopropylamines of formula $C_6H_5CH_2CH(CH_3)NHOR$ wherein R is $CH_3$, $C_2H_5$ or i-$C_3H_7$, and tested the compounds for MAO inhibitory activity.

Benington, F.; Morin, R. D. and Clark, L. C. Jr. (J. Med. Chem. 1965, 8, 100-104) described the synthesis of ring-substituted 1-aryl-2-hydroxyamino- and 1-aryl-2-methoxyamino-propanes and demonstrated that the compounds were general central stimulants.

Kende et al. described in Tetrahedron Letters 1991, 14, 1699-1702 the synthesis of hydroxylamino derivatives using samarium diiodide as reducing agent.

None of the above mentioned documents mentions the use of the compounds as inhibitors of protein and/or peptide fibrils aggregation.

WO99/62505 describes a method for the treatment of a neurodegenerative disorder comprising the administration of compounds able to inhibit the binding of an amyloid beta peptide to alpha-7 nicotinic acetylcholine receptors. This patent application claims compounds of the general formula:

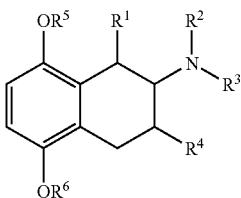

wherein $R^2$ is selected from hydrogen, $C_1$-$C_6$ alkyl, aryl or $C_7$-$C_{10}$ aralkyl and $R^3$ is selected from hydrogen, $C_1$-$C_6$ alkyl or $C_3$-$C_{10}$ alkenyl.

WO 01/30979 discloses pharmaceutical compositions comprising primary N-hydroxylamines of the general formula $NHOHCR_1R_2R_3$, wherein $R_1$, $R_2$ and $R_3$ are independently selected from hydrogen, substituted or unsubstituted ($C_1$-$C_{10}$) alkyl, alkenyl, alkynyl, aryl, acyl, carboxyl, amino, nitro, nitroso, oxime, hydrazone, azo, thiol, sulfonyl and halide and their use for reducing oxidative damage.

DESCRIPTION OF THE INVENTION

The present invention relates to the use of compounds of formula (I)

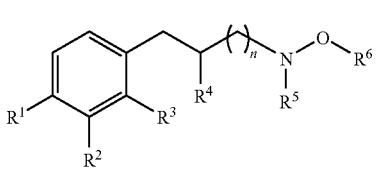

pharmaceutically acceptable salts or prodrugs thereof, wherein:
n is 0, 1 or 2;
$R^1$ and $R^2$, independently of each other, are H, OH or $OCH_3$;
$R^3$ is H or $CH_3$;
$R^4$ is H, $C_1$-$C_3$ straight or branched alkyl or, together with $R^3$, forms a five to seven-membered carbocyclic ring;
and $R^5$ and $R^6$, independently of each other, are H or $C_1$-$C_5$ straight or branched alkyl
for the preparation of pharmaceutical compositions for the prevention, treatment, diagnosis of central and peripheral nervous system disorders involving protein misfolding and/or misaggregation, for example disorders caused by formation of fibrils of beta-amyloid peptide, alpha-synuclein, prion protein and huntingtin, such as Alzheimer's Disease, Lewy body disease, Parkinson's Disease, spongiform encephalopathies, Huntington's Disease and systemic AA amyloidosis including the primary amyloidosis of the peripheral nervous system.

The invention also relates to compounds of formula (I) as defined above and pharmaceutically acceptable salts thereof with the provisos that:
$R^1$ and $R^2$ cannot be both hydrogen;
when n is 0, $R^1$ and $R^2$ are both hydroxyl, $R^3$ and $R^5$ are hydrogen, $R^4$ cannot be $CH_3$ (GB 1,062,299);
when n is 0, $R^3$ is H and $R^4$ is H or $CH_3$, $R^6$ cannot be $C_1$-$C_3$ straight or branched alkyl (U.S. 3,184,510);
and that the compounds cannot be:
1-(4-hydroxyphenyl)-2-hydroxylaminoethane, (J. Biol. Chem. 1979, 254, 8575-8583);
1-(4-hydroxyphenyl)-2-hydroxylaminopropane, (J. Pharm. Pharmac. 1973, 25, 708-717);
1-(4-methoxyphenyl)-2-hydroxylaminopropane, (J. Med. Chem. 1965, 8, 100-104, J. Pharm. Pharmac. 1973, 25, 708-717);
1-(3,4-dimethoxyphenyl)-2-hydroxylaminopropane, (J. Med. Chem. 1965, 8, 100-104, Tetrahedron 1975, 31, 1531-1535);
1-(4-methoxyphenyl)-4-hydroxylaminobutane, (Tetrahedron Letters 1991, 32, 1699-1702);
1-(3-methoxyphenyl)-2-hydroxylaminopropane, (Chem. Pharm. Bull. 1981, 29, 1615);
1-(3,4-dimethoxyphenyl)-2-hydroxylaminoethane, (WO92/00968);
N-methyl-1-(3,4-dihydroxyphenyl)-2-hydroxylaminopropane, (Xenobiotica 2003, 33, 1013);
1-(3-methoxy-4-hydroxyphenyl)-2-hydroxylaminopropane, (Xenobiotica 2003, 33, 1013);
N-methyl-1-(3-methoxy-4-hydroxyphenyl)-2-hydroxylaminopropane, (Xenobiotica 2003, 33, 1013);
N-methyl-1- (3,4-dimethoxyphenyl)-2-hydroxylaminopropane, (Tetrahedron 1975, 31, 2595).
Preferred novel compounds are:
N-(5-hydroxy-1,2,3,4-tetrahydro-naphthalen-2-yl)-O-methyl-hydroxylamine;
N-(5-hydroxy-1,2,3,4-tetrahydro-naphthalen-2-yl)-O-ethyl-hydroxylamine;
N-(5-hydroxy-1,2,3,4-tetrahydro-naphthalen-2-yl)-N-propyl-O-ethyl-hydroxylamine;
N-(5-methoxy-1,2,3,4-tetrahydro-naphthalen-2-yl)-O-methyl-hydroxylamine;
N-(5-methoxy-1,2,3,4-tetrahydro-naphthalen-2-yl)-O-ethyl-hydroxylamine;
N-(5-methoxy-1,2,3,4-tetrahydro-naphthalen-2-yl)-N-propyl-O-ethyl-hydroxylamine;
N-(5,6-dihydroxy-1,2,3,4-tetrahydro-naphthalen-2-yl)-O-methyl-hydroxylamine;
N-(5,6-dihydroxy-1,2,3,4-tetrahydro-naphthalen-2-yl)-O-ethyl-hydroxylamine;
N-(5,6-dihydroxy-1,2,3,4-tetrahydro-naphthalen-2-yl)-N-propyl-O-ethyl-hydroxylamine;
N-(5,6-dihydroxy-1,2,3,4-tetrahydro-naphthalen-2-yl)-N-butyl-O-ethyl-hydroxylamine;
N-(5,6-dihydroxy-1,2,3,4-tetrahydro-naphthalen-2-yl)-N-butyl-O-propyl-hydroxylamine;
N-(5,6-dimethoxy-1,2,3,4-tetrahydro-naphthalen-2-yl)-O-methyl-hydroxylamine;
N-(5,6-dimethoxy-1,2,3,4-tetrahydro-naphthalen-2-yl)-O-ethyl-hydroxylamine;
N-(5,6-dimethoxy-1,2,3,4-tetrahydro-naphthalen-2-yl)-N-propyl-O-ethyl-hydroxylamine;
N-(1-methyl-2-(3-hydroxy-phenyl)-ethyl)-hydroxylamine;
N-(1-methyl-2-(3-hydroxy-phenyl)-ethyl)-N-methyl-hydroxylamine;
N-(1-methyl-2-(3-hydroxy-phenyl)-ethyl)-N-propyl-hydroxylamine;
N-(1-methyl-2-(3,4-dihydroxy-phenyl)-ethyl)-N-propyl-hydroxylamine;
N-(1-methyl-2-(3-methoxy-phenyl)-ethyl)-N-methyl-hydroxylamine;
N-(1-methyl-2-(3-methoxy-phenyl)-ethyl)-N-propyl-hydroxylamine;
N-(1-methyl-2-(3,4-dimethoxy-phenyl)-ethyl)-hydroxylamine;
N-(1-methyl-2-(3,4-dimethoxy-phenyl)-ethyl)-N-propyl-hydroxylamine;

N-(5-hydroxy-1,2,3,4-tetrahydro-2-naphthalenyl-methyl)-O-ethyl-hydroxylamine;
N-(5-methoxy-1,2,3,4-tetrahydro-2-naphthalenyl-methyl)-O-ethyl-hydroxylamine;
N-(5,6-dihydroxy-1,2,3,4-tetrahydro-2-naphthalenyl-methyl)-O-ethyl-hydroxylamine;
N-(5,6-dimethoxy-1,2,3,4-tetrahydro-2-naphthalenyl-methyl)-O-ethyl-hydroxylamine;
N-(5-hydroxy-1,2,3,4-tetrahydro-2-naphthalenyl-methyl)-N-propyl-O-ethyl-hydroxylamine;
N-(5-methoxy-1,2,3,4-tetrahydro-2-naphthalenyl-methyl)-N-propyl-O-ethyl-hydroxylamine;
N-(5,6-dihydroxy-1,2,3,4-tetrahydro-2-naphthalenyl-methyl)-N-propyl-O-ethyl-hydroxylamine;
N-(5,6-dimethoxy-1,2,3,4-tetrahydro-2-naphthalenyl-methyl)-N-propyl-O-ethyl-hydroxylamine;
N-(2-methyl-3-(3,4-dihydroxy-phenyl)-propyl)-hydroxylamine;
N-(2-methyl-3-(3,4-dihydroxy-phenyl)-propyl)-O-ethyl-hydroxylamine;
N-(2-methyl-3-(3,4-dihydroxy-phenyl)-propyl)-N-methyl-hydroxylamine;
N-(2-methyl-3-(3,4-dihydroxy-phenyl)-propyl)-N-propyl-hydroxylamine;
N-(2-methyl-3-(3,4-dihydroxy-phenyl)-propyl)-N-propyl-O-ethyl-hydroxylamine;
N-(2-methyl-3-(3,4-dimethoxy-phenyl)-propyl)-hydroxylamine;
N-(2-methyl-3-(3,4-dimethoxy-phenyl)-propyl)-O-ethyl-hydroxylamine;
N-(2-methyl-3-(3,4-dimethoxy-phenyl)-propyl)-N-methyl-hydroxylamine;
N-(2-methyl-3-(3,4-dimethoxy-phenyl)-propyl)-N-propyl-hydroxylamine;
N-(2-methyl-3-(3,4-dimethoxy-phenyl)-propyl)-N-propyl-O-ethyl-hydroxylamine.

Preferred known compounds for the use of the invention are:
N-(1-methyl-2-(3-hydroxy-phenyl)-ethyl)-O-ethyl-hydroxylamine;
N-(1-methyl-2-(3-hydroxy-phenyl)-ethyl)-N-propyl-O-ethyl-hydroxylamine;
N-(1-methyl-2-(3,4-dihydroxy-phenyl)-ethyl)-hydroxylamine;
N-(1-methyl-2-(3,4-dihydroxy-phenyl)-ethyl)-O-ethyl-hydroxylamine;
N-(1-methyl-2-(3,4-dihydroxy-phenyl)-ethyl)-O-methyl-hydroxylamine;
N-(1-methyl-2-(3,4-dihydroxy-phenyl)-ethyl)-N-propyl-O-ethyl-hydroxylamine;
N-(1-methyl-2-(3-methoxy-phenyl)-ethyl)-O-ethyl-hydroxylamine;
N-(1-methyl-2-(3-methoxy-phenyl)-ethyl)-N-propyl-O-ethyl-hydroxylamine;
N-(1-methyl-2-(3,4-dimethoxy-phenyl)-ethyl)-O-ethyl-hydroxylamine;
N-(1-methyl-2-(3,4-dimethoxy-phenyl)-ethyl)-N-propyl-O-ethyl-hydroxylamine;

The present invention includes all the possible optical isomers of the compounds of formula (I) and their mixtures, as well as their metabolites. Some crystalline forms of the compounds may exist as polymorphs, which are also included in the present invention. Some of the compounds are solvated with water, and as such they are also intended to be encompassed within the scope of the invention. The invention also includes pharmaceutically acceptable bioprecursors and prodrugs of compounds of formula (I). Selection and preparation of prodrugs are described, for example, in "Design of Prodrugs", ed. H. Bundgaard, Elsevier, 1985.

Suitable pharmaceutically acceptable salts of compounds of formula (I) include acid addition salts with inorganic acids, e.g. nitric, hydrochloric, carbonic, hydrobromic, sulphuric and phosphoric acid, or with organic acids, e.g. acetic, propionic, glycolic, lactic, oxalic, malonic, succinic, maleic, fumaric, tartaric, citric, benzoic, cinnamic, mandelic, methanesulphonic, salicylic acid.

The compounds of the invention can be prepared by different methods.

According to a first method, a compounds of formula (II)

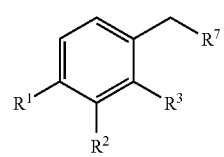

(II)

wherein $R^1$, $R^2$, $R^3$ are as defined above and $R^7$ is —C(=O)$R^4$, —CH($R^4$)—CHO, or —CH($R^4$)—CH$_2$—CHO, wherein $R_4$ is as defined above is reacted with a compound of formula (III)

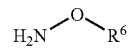

(III)

wherein $R^6$ is as defined above, in the presence of a reducing agent to give a compound of formula (I) wherein $R^5$ is hydrogen. This is subsequently alkylated with a compound of formula (IV):

(IV)

wherein $R^5$ is $C_1$-$C_5$ straight or branched alkyl and X is a halogen atom or a leaving group, preferably selected from mesylate, tosylate or triflate.

Alternatively, compounds of formula (I) wherein $R^5$ is hydrogen can be subjected to reductive alkylation with a compound of formula (V):

(V)

wherein $R^8$ is hydrogen or $C_1$-$C_4$ alkyl.

Compounds of formula (I) wherein $R^5$ is hydrogen can also be obtained by reacting a compound of formula (VI)

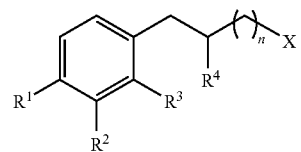

(VI)

wherein n, $R^1$, $R^2$, $R^3$, $R^4$ and X are as defined above
with a compound of formula (VII)

(VII)

wherein $R^6$ is as defined above in the presence of a base and subsequent hydrolysis of the resulting carbamate.

According to a further method, a compound of formula (VIII)

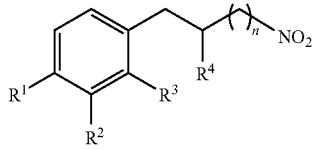

wherein n, $R^1$, $R^2$, $R^3$ and $R^4$ are as defined above,
is reduced with $BH_3 \cdot THF$, $NaBH_4$, $Zn/NH_4Cl$, $SmI_2$ (Kende, A. S. and Mendoza, J. S. *Tetrahedron Letters* 1991, 32, 1699-1702), to give compounds of formula (I) where both $R_5$ and $R_6$ are hydrogen. N- and/or O-alkylation can be performed according to methods described in the literature and well known to those skilled in the art.

The compounds of the general formula (I) wherein both $R^5$ and $R^6$ are hydrogen can also be obtained by alkylation of the amino group of compounds of general formula (IX)

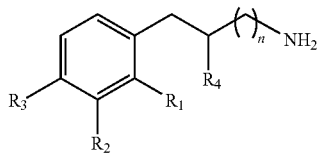

wherein n, $R^1$, $R^2$, $R^3$ and $R^4$ are as defined above
with $YCH_2CN$ (with Y=Cl, Br, I), oxidation with m-CPBA, and subsequent hydrolysis with hydroxylamine (H. Tokuyama et al. *Synthesis* 2000, 9, 1299-1304).

Compounds (II), (III), (IV), (V), (VI), (VII), (VIII) and (IX) are commercially available or can be prepared from commercially available compounds by conventional methods.

Reductive amination is preferably performed under nitrogen atmosphere, in a suitable organic solvent, preferably an alcohol, at a temperature ranging from about 0° C. to about 40° C. The reduction can be carried out with hydrides, preferably selected from $NaBH_4$, $NaBH_3CN$ or by catalytic hydrogenation, the most appropriate catalyst being $PtO_2$. Molecular sieves can optionally be added to the reaction mixture to promote the reaction.

The reaction of compounds of formula (VI) with compounds of formula (VII) is carried out in alkaline conditions, in solvents like alcohols, THF, acetonitrile, at temperatures ranging from room temperature to 100° C.

In compounds of the general formulas (IV) and (VI), X is preferably iodine or mesylate and alkylation can be carried out in a suitable organic solvent, preferably selected from methanol, ethanol or isopropanol, more preferably ethanol, at a temperature ranging from about 0° C. to about 50° C.

The reductive alkylation of compounds of formula (I) wherein $R_5$ is hydrogen with an aldehyde of formula (V) can be carried out in a suitable organic solvent, such as an alcohol, e.g. methanol, ethanol or acetonitrile in the presence of a suitable reducing agent, such as sodium cyanoborohydride, at a temperature ranging from about 0° C. to about 30° C.

The reduction of the nitro group of compounds of the general formula (VII) to hydroxylamino group can be carried out according to conventional methods, preferably under nitrogen atmosphere with diborane or $NaBH_4$ in THAF at a temperature ranging from about 0° C. to about 25° C., or with $SmI_2$ in THF/methanol at room temperature.

The oxidation of compounds of the general formula (IX) can be carried out according to Tokuyama, H. et al. Compounds of the general formula (IX) are first treated with Y—$CH_2CN$, in a suitable organic solvent, preferably acetonitrile or DMF, with a suitable base, preferably Hünig's base (N,N-diisopropylethylamine) or $K_2CO_3$ and subsequently oxidised with m-CPBA in a suitable organic solvent, preferably $CH_2Cl_2$, at a temperature ranging from room temperature to 40° C.; the final treatment with hydroxylamine is carried out in an alcoholic solvent, preferably in boiling methanol.

PHARMACOLOGY

The compounds of the invention are able to interfere with the in vitro aggregation, fibrilization and deposition of different types of self-aggregating proteins, such as Amyloid-$\beta_{1-42}$, Prion Protein$_{106-126}$ and α-synuclein.

In our experimental conditions, the peptide monomer (anti-aggregation protocol) or already aggregated (disaggregation protocol) was incubated at 37° C., alone or in the presence of the test compound, for different time intervals, then centrifuged and both the supernatant and the pellet were analyzed by HPLC or Thioflavine T binding assay.

The potencies of the compounds of this invention in inhibiting the aggregation or in inducing the disaggregation of the fibrils are in low μMolar range and at least in 1:10 molar ratio to the peptide concentration.

As shown in Table 1, the compound N-(1-methyl-2-(3,4-dihydroxy-phenyl)-ethyl)-O-methyl-hydroxylamine (1) and the compound N-(5,6-dihydroxy-1,2,3,4-tetrahydro-naphthalene-2-yl)-N-propyl-O-ethyl-hydroxylamine (2) display significant anti-aggregating properties against the all three proteins tested (A$\beta_{1-42}$, PrP$_{106-126}$ and α-synuclein). As compared to the known compound trans-N-(5,8-hydroxy-3-methyl-1,2,3,4-tetrahydro-naphtalene-2yl)-N,N-dipropyl-amine (3), described in WO99/62505 and Bioorg.Med.Chem. 10 (2002) 3565-3569, compound (2) is significantly more potent in inhibiting the aggregation of all three proteins, whears compound (1) is more potent in inhibiting the aggregation of A$\beta_{1-42}$ and α-synuclein and equally potent in inhibiting PrP$_{106-126}$ fibrils.

TABLE 1

In vitro Amyloid-$\beta_{1-42}$, Prion Protein$_{106-126}$ and α-synuclein fibril formation

| Compound | β-Amyloid$_{1-42}$ Anti-aggregation (HPLC assay) IC$_{50}$*, μM | PrP$_{106-126}$ Anti-aggregation (HPLC assay) IC$_{50}$, μM | α-synuclein Anti-aggregation (HPLC assay) IC$_{50}$, μM |
|---|---|---|---|
| 1 | 15 | 76 | 222 |
| 2 | 6 | 20 | 35 |
| 3 | 60 | 75 | 878 |

*IC$_{50}$ = Concentration able to inhibit the aggregation of the fibrils by 50%

Pharmaceutical compositions of compounds of formula (I) for oral, parenteral, rectal, sublingual, intranasal or transdermal administration can be prepared according to conventional methods and with conventional excipients or carriers, for example as disclosed in Remington's Pharmaceutical Sciences Handbook, XVII ed., Mack Pub., N.Y., U.S.A. The effective dose ranges from 0.1 mg/Kg and 100 mg/Kg. Optimal dosages may be determined by those skilled in the art, and will vary according to the compound, the administration route and the development of the disease. Patient-associated parameters, such as body weight, age, sex, diet, physical activity, period of administration, associated co-morbidities and clinical conditions will also be taken into account.

Preferred pharmaceutical compositions for oral administration are preferably tablets, sublingual tablets, compressed or coated pills, dragees, sachets, hard or soft gelatine capsules. Suitable excipients or carriers include diluents, preferably lactose, dextrose, sucrose, mannitol, sorbitol, cellulose; lubricants, preferably silica, talc, stearic acid, magnesium or calcium stearate, and/or polyethylene glycols; binders, preferably starches, gelatine, methylcellulose, carboxymethylcellulose, arabic gum, tragacanth, polyvinylpyrrolidone; disgregants, preferably starches, alginic acid, alginates, sodium starch glycolate; effervescing mixtures; dyestuffs; sweeteners; wetting agents, preferably lecithin, polysorbates, laurylsulphates; and, in general, non-toxic.

Liquid dispersions for oral administration are preferably syrups, emulsions, and suspensions. Suitable carriers for syrups include saccharose or saccharose in admixture with glycerine and/or mannitol and/or sorbitol. Suitable carriers for suspensions and emulsions include natural gums, agar, sodium alginate, pectin, methylcellulose, carboxymethylcellulose, or polyvinyl alcohol. Suitable carriers for suspensions or solutions for intramuscular injections include preferably sterile water, olive oil, ethyl oleate, glycols, e.g. propylene glycol. A suitable amount of lidocaine hydrochloride can optionally be contained in injectable preparations.

Suitable carriers solutions for intravenous injection or infusion are sterile water or sterile isotonic saline.

Suitable excipients for suppositories include cocoa butter, polyethylene glycol, polyoxyethylene sorbitan fatty acid ester surfactants or lecithins.

The following examples illustrate the invention in greater detail.

EXAMPLE 1

N-(5,6-Dimethoxy-1,2,3,4-tetrahydro-naphthalen-2-yl)-O-ethyl-hydroxylamine 5,6-Dimethoxy-3,4-dihydro-1H-naphthalen-2-one (1.5 g, 7.5 mmol), prepared as described in *J Med. Chem.* 1977, 20, 1111-1116, was dissolved in water (15 ml) and a solution of O-ethylhydroxylamine hydrochloride (1 g, 10 mmol) and $Na_2CO_3$ (0.53 g, 5 mmol) in water (10 ml) was added dropwise under stirring at 10° C. The reaction was left at room temperature overnight and then extracted with diethyl ether. The ether solution was evaporated to dryness under vacuum. The residue was dissolved in 20 ml of ethanol and concentrated hydrochloric acid (1 ml) and hydrogenated at $3,6 \times 10^6$ Pa (50 psi) using $PtO_2$ as catalyst. The solvent was removed under reduced pressure, water was added and the aqueous phase was treated with $NaHCO_3$ and extracted with ethyl acetate. The organic phase was dried over $MgSO_4$, filtered and concentrated to dryness under vacuum. The crude residue was purified by chromatography, to afford 0.85 g of the title compound.

MS (EI): 251.0 ($M^{30}$).

EXAMPLE 2

N-(5,6-Dimethoxy-1,2,3,4-tetrahydro-naphthalen-2-yl)-N-propyl-O-ethyl-hydroxylamine N-(5,6-Dimethoxy-1,2,3,4-tetrahydro-naphthalen-2-yl)-O-ethyl-hydroxylamine (0.85 g, 3.4 mmol), obtained as described in Example 1, was dissolved in 2-pentanone (10 ml) and refluxed with 1-bromopropane (0.5 g, 4 mmol) and solid $K_2CO_3$ (0.6 g, 4.5 mmol). The solid was filtered and the solvent was evaporated to dryness under vacuum. The crude residue (1.2 g) was purified by chromatography to afford 0.28 g of the title compound.

MS (EI): 293.2 ($M^+$).

EXAMPLE 3

N-(5,6-Dihydroxy-1,2,3,4-tetrahydro-naphthalen-2-yl)-N-propyl-O-ethyl-hydroxylamine N-(5,6-Dimethoxy-1,2,3,4-tetrahydro-naphthalen-2-yl)-N-propyl-O-ethyl-hydroxylamine (0.8 g, 2.7 mmol), obtained as described in Example 2, was dissolved in 48% HBr (12 ml) and refluxed until completion of the reaction. The solvent was evaporated to dryness under vacuum and the residue was purified by chromatography ($CH_2Cl_2$/MeOH 90:10) to afford 0.5 g of the title compound.

MS (EI): 265.2 ($M^+$);

$^1$H-NMR (DMSO+TFA) δ: 6.62 (d, 1H); 6.41 (d, 1H); 4.07 (q, 2H); 3.50-3.62 (m, 1H); 3.18-3.27 (m, 2H); 2.70-3.01 (m, 3H); 2.18-2.30 (m, 1H); 1.61-1.76 (m, 3H); 1.15 (t, 3H); 0.92 (t, 3H).

The following compounds are obtained according to the same procedures described in examples 1-3:
 N-(5-hydroxy-1,2,3,4-tetrahydro-naphthalen-2-yl)-O-methyl-hydroxylamine;
 N-(5-hydroxy-1,2,3,4-tetrahydro-naphthalen-2-yl)-O-ethyl-hydroxylamine;
 N-(5-hydroxy-1,2,3,4-tetrahydro-naphthalen-2-yl)-N-propyl-O-ethyl-hydroxylamine;
 N-(5-methoxy-1,2,3,4-tetrahydro-naphthalen-2-yl)-O-methyl-hydroxylamine;
 N-(5-methoxy-1,2,3,4-tetrahydro-naphthalen-2-yl)-O-ethyl-hydroxylamine;
 N-(5-methoxy-1,2,3,4-tetrahydro-naphthalen-2-yl)-N-propyl-O-ethyl-hydroxylamine;
 N-(5,6-dihydroxy-1,2,3,4-tetrahydro-naphthalen-2-yl)-O-methyl-hydroxylamine;
 N-(5,6-dihydroxy-1,2,3,4-tetrahydro-naphthalen-2-yl)-O-ethyl-hydroxylamine;
 N-(5,6-dimethoxy-1,2,3,4-tetrahydro-naphthalen-2-yl)-O-methyl-hydroxylamine;
 N-(5-hydroxy-1,2,3,4-tetrahydro-2-naphthalenyl-methyl)-O-ethyl-hydroxyl amine;
 N-(5-methoxy-1,2,3,4-tetrahydro-2-naphthalenyl-methyl)-O-ethyl-hydroxylamine;
 N-(5,6-dihydroxy-1,2,3,4-tetrahydro-2-naphthalenyl-methyl)-O-ethyl-hydroxylamine;
 N-(5,6-dimethoxy-1,2,3,4-tetrahydro-2-naphthalenyl-methyl)-O-ethyl-hydroxyl amine;
 N-(5-hydroxy-1,2,3,4-tetrahydro-2-naphthalenyl-methyl)-N-propyl-O-ethyl-hydroxylamine;
 N-(5-methoxy-1,2,3,4-tetrahydro-2-naphthalenyl-methyl)-N-propyl-O-ethyl-hydroxylamine;,
 N-(5,6-dihydroxy-1,2,3,4-tetrahydro-2-naphthalenyl-methyl)-N-propyl-O-ethyl-hydroxylamine;
 N-(5,6-dimethoxy-1,2,3,4-tetrahydro-2-naphthalenyl-methyl)-N-propyl-O-ethyl-hydroxylamine.

EXAMPLE 4

N-(1-Methyl-2-(3,4-dimethoxy-phenyl)-ethyl)-O-ethyl-hydroxylamine 1-(3,4-Dimethoxyphenyl)-2-propanone (1.35 g, 7.5 mmol) was dissolved in $H_2O$ (15 ml) and a solution of O-ethylhydroxylamine hydrochloride (1 g, 10 mmol) and Na$_2$CO$_3$ (0.53 g, 5 mmol) in water (10 ml) was added dropwise under stirring at 10° C. The reaction was left at room temperature overnight and then extracted with diethyl ether. After evaporation of the solvent, the residue was dissolved in EtOH (20 ml) and concentrated hydrochloric acid (1 ml), then hydrogenated over PtO$_2$ at 3,6×10$^6$ Pa (50 psi). The solvent was removed under vacuum. The residue was dissolved in 30 ml of water, the aqueous phase was made basic with NaHCO$_3$ and extracted with ethyl acetate. The organic phase was dried over MgSO$_4$, filtered and concentrated to dryness. The crude residue was purified by flash chromatography, to afford 0.75 g of the title compound.

MS (EI): 239.3 (M$^+$).

EXAMPLE 5

N-(1-Methyl-2-(3,4-dimethoxy-phenyl)-ethyl)-N-propyl-O-ethyl-hydroxylamine

N-(1-Methyl-2-(3,4-dimethoxy-phenyl)-ethyl)-O-ethyl-hydroxylamine (0.3 g, 1 mmol), obtained as described in Example 4, was dissolved in acetonitrile (10 ml) and refluxed with 1-bromopropane (0.135 g, 1.1 mmol) and solid K$_2$CO$_3$ (0.83 g, 6 mmol). The solid was filtered and the solvent was evaporated to dryness under vacuum. The crude residue (0.4 g) was purified by flash chromatography to afford 0.25 g of the title compound.

MS (EI): 281.3 (M$^+$).

EXAMPLE 6

N-(1-Methyl-2-(3,4-dihydroxy-phenyl)-ethyl)-N-propyl-O-ethyl-hydroxylamine

N-(1-Methyl-2-(3,4-dimethoxy-phenyl)-ethyl)-N-propyl-O-ethyl-hydroxylamine 0.25 g, 0.9 mmol), obtained as described in Example 5, was dissolved in 48% HBr (4 ml) and refluxed until completion of the reaction. The solvent was evaporated to dryness under vacuum and the crude residue was purified by chromatography (CH$_2$Cl$_2$/MeOH 90:10) to afford 0.16 g of the title compound.

MS (EI): 253.3 (M$^+$);

$^1$H-NMR (DMSO) δ: 6.62 (d, 1H); 6.56 (s, 1H); 6.41 (d, 1H); 3.73 (q, 2H); 2.92-3.08 (m, 1H); 2.80-2.88 (m, 1H); 2.61-2.73 (m, 2H); 2.18-2.28 (m, 1H); 1.45-2.58 (m, 2H); 1.08 (t, 3H); 0.86-0.95 (m, 6H).

Anal. (C$_{14}$H$_{23}$NO$_3$·C$_2$HF$_3$O$_2$) C, H, N and F.

The following compounds are obtained according to the same procedures described in examples 4-6:

N-(1-methyl-2-(3-hydroxy-phenyl)-ethyl)-hydroxylarnine;
N-(1-methyl-2-(3-hydroxy-phenyl)-ethyl)-O-ethyl-hydroxylamine;
N-(1-methyl-2-(3-hydroxy-phenyl)-ethyl)-N-methyl-hydroxylamine;
N-(1-methyl-2-(3-hydroxy-phenyl)-ethyl)-N-propyl-hydroxylamine;
N-(1-methyl-2-(3-hydroxy-phenyl)-ethyl)-N-propyl-O-ethyl-hydroxylamine;
N-(1-methyl-2-(3,4-dihydroxy-phenyl)-ethyl)-hydroxylamine;
N-(1-methyl-2-(3,4-dihydroxy-phenyl)-ethyl)-O-ethyl-hydroxylamine;
N-(1-methyl-2-(3,4-dihydroxy-phenyl)-ethyl)-O-methyl-hydroxylamine;
N-(1-methyl-2-(3,4-dihydroxy-phenyl)-ethyl)-N-propyl-hydroxylamine;
N-(1-methyl-2-(3-methoxy-phenyl)-ethyl)-O-ethyl-hydroxylamine;
N-(1-methyl-2-(3-methoxy-phenyl)-ethyl)-N-methyl-hydroxylamine;
N-(1-methyl-2-(3-methoxy-phenyl)-ethyl)-N-propyl-hydroxylamine;
N-(1-methyl-2-(3-methoxy-phenyl)-ethyl)-N-propyl-O-ethyl-hydroxylamine;
N-(1-methyl-2-(3,4-dimethoxy-phenyl)-ethyl)-hydroxylamine;
N-(1-methyl-2-(3,4-dimethoxy-phenyl)-ethyl)-N-propyl-hydroxylamine;
N-(2-methyl-3-(3,4-dihydroxy-phenyl)-propyl)-hydroxylamine;
N-(2-methyl-3-(3,4-dihydroxy-phenyl)-propyl)-O-ethyl-hydroxylamine;
N-(2-methyl-3-(3,4-dihydroxy-phenyl)-propyl)-N-methyl-hydroxylamine;
N-(2-methyl-3-(3,4-dihydroxy-phenyl)-propyl)-N-propyl-hydroxylamine;
N-(2-methyl-3-(3,4-dihydroxy-phenyl)-propyl)-N-propyl-O-ethyl-hydroxylamine;
N-(2-methyl-3-(3,4-dimethoxy-phenyl)-propyl)-hydroxylamine;
N-(2-methyl-3-(3,4-dimethoxy-phenyl)-propyl)-O-ethyl-hydroxyl amine;
N-(2-methyl-3-(3,4-dimethoxy-phenyl)-propyl)-N-methyl-hydroxylamine;
N-(2-methyl-3-(3,4-dimethoxy-phenyl)-propyl)-N-propyl-hydroxylamine;
N-(2-methyl-3-(3,4-dimethoxy-phenyl)-propyl)-N-propyl-O-ethyl-hydroxylamine.

EXAMPLE 7

Inhibition of Aβ 1-42 Spontaneous Aggregation

Preparation of the Aβ 1-42 peptide

Synthetic Aβ 1-42 (U.S. Peptide, Rancho Cucamonga, USA) was dissolved to 220 μM in H$_2$O/CH$_3$CN 1:1. Aliquots of 10 μg were lyophilized under vacuum with an Eppendorf concentrator for 18 h and stored at −80° C.

Aβ 1-42 spontaneous aggregation

10 μg of lyophilized peptide sample was dissolved at 20 μM in 20 mM potassium phosphate buffer, pH 7.4, containing 150 mM NaCl. The sample was incubated for 18 h at 37° C. After centrifugation at 13000 xg for 5 min, the pellet was dissolved in formic acid and both the pellet and the supernatant were analysed by HPLC. The extent of aggregation was determined as the percentage of peptide content in the pellet compared with the total amount.

| HPLC analysis of the Aβ 1-42 peptide monomer | |
|---|---|
| Column: | PLRP-S 100 Å, 8 μm, 150 × 4.6 mm, Polymer Laboratories |
| Mobile phase: | gradient from 15% A to 70% B in 10 min<br>A = H$_2$O + 0.01% TFA<br>B = CH$_3$CN + 0.08% TFA |
| Flow rate: | 0.7 ml/min |
| Detector: | UV, 214 nm |

EXAMPLE 8

Inhibition of Non Aβ Component of Alzheimer's Disease Amyloid (NAC, α-synuclein) Spontaneous Aggregation Preparation of the NAC peptide The synthetic peptide NAC (Bachem) was dissolved at 1 mg/ml in $H_2O/CH_3CN$ 1:1 plus 5% TFA. Aliquots of 40 μg were lyophilized under vacuum for 18 h and stored at −80° C.

NAC spontaneous aggregation

40 μg of lyophilized peptide sample was dissolved at 500 μM in 20 mM potassium phosphate buffer, pH 7.4, containing 150 mM NaCl. The sample was incubated for 24 h at 37° C. After centrifugation at 13000 xg for 5 min, the pellet was dissolved in formic acid and both pellet and supernatant were analyzed by HPLC. The extent of aggregation was determined as the percentage of peptide content in the pellet compared to the total amount used.

| HPLC analysis of the NAC peptide monomer | |
|---|---|
| | 1 pump |
| | 1 autosampler |
| | 1 UV detector |
| Guard column: | high performance guard column, 5 μm, Vydac |
| Column: | Protein and Peptide C18, 5 μm, 25 × 0.46 cm, Vydac |
| Mobile phase: | gradient developed from 95% A to 100% B in 12 min |
| | A = $H_2O$ + 0.1% TFA |
| | B = $CH_3CN$ + 0.08% TFA |
| Flow rate: | 1 ml/min |
| Detector: | UV, 214 nm |

EXAMPLE 9

Inhibition of PrP 106-126 Spontaneous Aggregation

Preparation of the Prp 106-126 peptide

The synthetic peptide PrP 106-126 (Bachem) was dissolved at 1 mg/ml in $H_2O/CH_3CN$ 1:1. Aliquots of 30 μg were lyophilized under vacuum for 18 h and stored at −80° C.

PrP 106-126 spontaneous aggregation

30 μg of lyophilized peptide sample was dissolved at 500 μM in 20 mM potassium phosphate buffer, pH 7.4, containing 150 mM NaCl. The sample was incubated for 24 h at 37° C. After centrifugation at 13000 xg for 5 min, the pellet was dissolved in formic acid and both pellet and supernatant were analyzed by HPLC. The extent of aggregation was determined as the percentage of peptide content in the pellet compared to the total amount used.

| HPLC analysis of the PrP 106-126 peptide monomer | |
|---|---|
| | 1 pump |
| | 1 autosampler |
| | 1 UV detector |
| Guard column: | high performance guard column, 5 μm, Vydac |
| Column: | Protein and Peptide C18, 5 μm 25 × 0.46 cm, Vydac |
| Mobile phase: | gradient developed from 95% A to 70% B in 12 min |
| | A = $H_2O$ + 0.1% TFA |
| | B = $CH_3CN$ + 0.08% TFA |
| Flow rate: | 1 ml/min |
| Detector: | UV, 214 nm |

EXAMPLE 10

Thioflavine T (ThT) Binding Assay

After aggregation, the sample was centrifuged and the supernatant was discarded. The pellet was resuspended in 300 μl of 50 mM glycine-NaOH buffer, pH 9.4 containing 2 μM ThT and incubated for 5 min. The fluorescence was determined by a fluorescence plate reader (Fusion, Packard) at a 400 nm excitation wavelength and a 485 nm emission wavelength.

The invention claimed is:
1. A compound of the formula:

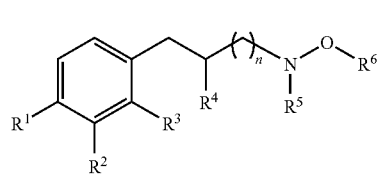

(I)

and pharmaceutically acceptable salts thereof, wherein n, $R^1$, $R^2$, $R^3$, $R^4$, $R^5$ and $R^6$ are chosen such that the compound is selected from the group consisting of:

N-(5-hydroxy-1,2,3,4-tetrahydro-naphthalen-2-yl)-O-methyl-hydroxylamine;
N-(5-hydroxy-1,2,3,4-tetrahydro-naphthalen-2-yl)-hydroxylamine;
N-(5-hydroxy-1,2,3,4-tetrahydro-naphthalen-2-yl)-N-propyl-O-ethyl-hydroxylamine;
N-(5-methoxy-1,2,3,4-tetrahydro-naphthalen-2-yl)-O-methyl-hydroxylamine;
N-(5-methoxy-1,2,3,4-tetrahydro-naphthalen-2-yl)-O-ethyl-hydroxylamine;
N-(5-methoxy-1,2,3,4-tetrahydro-naphthalen-2-yl)-N-propyl-O-ethyl-hydroxylamine;
N-(5,6-dihydroxy-1,2,3,4-tetrahydro-naphthalen-2-yl)-O-methyl-hydroxylamine;
N-(5,6-dihydroxy-1,2,3,4-tetrahydro-naphthalen-2-yl)-O-ethyl-hydroxylamine;
N-(5,6-dihydroxy-1,2,3,4-tetrahydro-naphthalen-2-yl)-N-propyl-O-ethyl-hydroxylamine;
N-(5,6-dihydroxy-1,2,3,4-tetrahydro-naphthalen-2-yl)-N-butyl-O-ethyl-hydroxylamine;
N-(5,6-dihydroxy-1,2,3,4-tetrahydro-naphthalen-2-yl)-N-butyl-O-propyl-hydroxylamine;
N-(5,6-dimethoxy-1,2,3,4-tetrahydro-naphthalen-2-yl)-O-methyl-hydroxylamine;
N-(5,6-dimethoxy-1,2,3,4-tetrahydro-naphthalen-2-yl)-O-ethyl-hydroxylamine;
N-(5,6-dimethoxy-1,2,3,4-tetrahydro-naphthalen-2-yl)-N-propyl-O-ethyl-hydroxylamine;
N-(1-methyl-2-(3-hydroxy-phenyl)-ethyl)-hydroxylamine;
N-(1-methyl-2-(3-hydroxy-phenyl)-ethyl)-N-methyl-hydroxylamine;
N-(1-methyl-2-(3-hydroxy-phenyl)-ethyl)-N-propyl-hydroxylamine;
N-(1-methyl-2-(3,4-dihydroxy-phenyl)-ethyl)-N-propyl-hydroxylamine;
N-(1-methyl-2-(3-methoxy-phenyl)-ethyl)-N-methyl-hydroxylamine;
N-(1-methyl-2-(3-methoxy-phenyl)-ethyl)-N-propyl-hydroxylamine; hydroxylamine;

N-(1-methyl-2-(3,4-dimethoxy-phenyl)-ethyl)-N-propyl-hydroxylamine;
N-(5-hydroxy-1,2,3,4-tetrahydro-2-naphthalenyl-methyl)-O-ethyl-hydroxylamine;
N-(5-methoxy-1,2,3,4-tetrahydro-2-naphthalenyl-methyl)-O-ethyl-hydroxylamine;
N-(5,6-dihydroxy-1,2,3,4-tetrahydro-2-naphthalenyl-methyl)-O-ethyl-hydroxylamine;
N-(5,6-dimethoxy-1,2,3,4-tetrahydro-2-naphthalenyl-methyl)-O-ethyl-hydroxylamine;
N-(5-hydroxy-1,2,3,4-tetrahydro-2-naphthalenyl-methyl)-N-propyl-O-ethyl-hydroxylamine;
N-(5-methoxy-1,2,3,4-tetrahydro-2-naphthalenyl-methyl)-N-propyl-O-ethyl-hydroxylamine;
N-(5,6-dihydroxy-1,2,3,4-tetrahydro-2-naphthalenyl-methyl)-N-propryl-O-ethyl-hydroxylamine;
N-(5,6-dimethoxy-1,2,3,4-tetrahydro-2-naphthalenyl-methyl)-N-propyl-O-ethyl-hydroxylamine;
N-(2-methyl-3-(3,4-dihydroxy-phenyl)-propyl)-hydroxylamine;
N-(2-methyl-3-(3,4-dihydroxy-phenyl)-propyl)-O-ethyl-hydroxylamine;
N-(2-methyl-3-(3,4-dihydroxy-phenyl)-propyl)-N-methyl-hydroxylamine;
N-(2-methyl-3-(3,4-dihydroxy-phenyl)-propyl)-N-propyl-hydroxylamine;
N-(2-methyl-3-(3,4-dihydroxy-phenyl)-propyl)-N-propyl-O-ethyl-hydroxylamine;
N-(2-methyl-3-(3,4-dimethoxy-phenyl)-propyl)-hydroxylamine;
N-(2-methyl-3-(3,4-dimethoxy-phenyl)-propyl)-O-ethyl-hydroxylamine;
N-(2-methyl-3-(3,4-dimethoxy-phenyl)-propyl)-N-methyl-hydroxylamine;
N-(2-methyl-3-(3,4-dimethoxy-phenyl)-propyl)-N-propyl-hydroxylamine;
N-(2-methyl-3-(3,4-dimethoxy-phenyl)-propyl)-N-propyl-O-ethyl-hydroxylamine; and
the pharmaceutically acceptable salts thereof.

2. A pharmaceutical composition comprising one or more compounds according to claim 1 in a mixture with suitable excipients and/or carriers.

3. A pharmaceutical composition comprising one or more compounds according to claim 1 and a compound for the treatment of central and peripheral nervous system disorders involving protein misfolding and/or misaggregation of beta-amyloid peptide, alpha-synuclein, prion protein and huntingtin selected from Alzheimer's Disease, Lewy body disease, Parkinson's Disease, spongiform encephalopathies, Huntington's Disease and systemic AA amyloidosis, in admixture with suitable excipients and/or carriers.

* * * * *